(12) United States Patent
Ellis et al.

(10) Patent No.: US 10,080,516 B2
(45) Date of Patent: *Sep. 25, 2018

(54) BIOLOGICAL FLUID COLLECTION DEVICE AND BIOLOGICAL FLUID SEPARATION AND TESTING SYSTEM

(71) Applicant: Becton, Dickinson and Company, Franklin Lakes, NJ (US)

(72) Inventors: Robert G. Ellis, Wayne, NJ (US); Bradley M. Wilkinson, North Haledon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 601 days.

This patent is subject to a terminal disclaimer.

(21) Appl. No.: 14/251,686

(22) Filed: Apr. 14, 2014

(65) Prior Publication Data

US 2014/0305196 A1 Oct. 16, 2014

Related U.S. Application Data

(60) Provisional application No. 61/811,918, filed on Apr. 15, 2013.

(51) Int. Cl.
*A61B 5/15* (2006.01)
*G01N 33/49* (2006.01)
(Continued)

(52) U.S. Cl.
CPC ...... *A61B 5/150213* (2013.01); *A61B 5/1411* (2013.01); *A61B 5/151* (2013.01);
(Continued)

(58) Field of Classification Search
USPC ..................... 73/64.56; 210/321.72
See application file for complete search history.

(56) References Cited

U.S. PATENT DOCUMENTS 3,159,159 A * 12/1964 Cohen ............... A61B 5/15003
251/353
3,322,114 A 5/1967 Portnoy et al.
(Continued)

FOREIGN PATENT DOCUMENTS

CN 1169886 A 1/1998
CN 1382966 A 12/2002
(Continued)

OTHER PUBLICATIONS

Membrane Separation Technology for Research and Quality Control, Sartorius AG, Separation Technology, Laboratory Filtration; Mar. 1, 1977.

*Primary Examiner* — Son Le
*Assistant Examiner* — Marrit Eyassu
(74) *Attorney, Agent, or Firm* — The Webb Law Firm (57) ABSTRACT

A biological fluid collection device that is adapted to receive a blood sample having a cellular portion and a plasma portion is disclosed. After collection of the blood sample, the plasma portion is separated from the cellular portion. After separation, the biological fluid collection device is able to transfer the plasma portion of the blood sample to a point-of-care testing device. The biological fluid collection device also provides a closed sampling and transfer system that reduces the exposure of a blood sample and provides fast mixing of a blood sample with a sample stabilizer. The biological fluid collection device is engageable with a biological fluid testing device for closed transfer of a portion of the plasma portion from the biological fluid collection device to the biological fluid testing device. The biological fluid testing device is adapted to receive the plasma portion to analyze the blood sample.

26 Claims, 10 Drawing Sheets (51) Int. Cl.

| | | |
|---|---|---|
| *A61M 1/34* | (2006.01) | |
| *G01N 1/28* | (2006.01) | |
| *G01N 1/40* | (2006.01) | |
| *G01N 1/34* | (2006.01) | |
| *B01L 3/00* | (2006.01) | |
| *B04B 7/08* | (2006.01) | |
| *A61B 5/151* | (2006.01) | |
| *A61B 5/157* | (2006.01) | |

(52) U.S. Cl.
CPC ........ *A61B 5/157* (2013.01); *A61B 5/150022* (2013.01); *A61B 5/15101* (2013.01); *A61B 5/15105* (2013.01); *A61B 5/15144* (2013.01); *A61B 5/15198* (2013.01); *A61B 5/150221* (2013.01); *A61B 5/150267* (2013.01); *A61B 5/150305* (2013.01); *A61B 5/150343* (2013.01); *A61B 5/150351* (2013.01); *A61B 5/150412* (2013.01); *A61B 5/150748* (2013.01); *A61B 5/150755* (2013.01); *A61B 5/150778* (2013.01); *A61M 1/34* (2013.01); *B01L 3/502* (2013.01); *B01L 3/5021* (2013.01); *B04B 7/08* (2013.01); *G01N 1/28* (2013.01); *G01N 1/34* (2013.01); *G01N 1/4005* (2013.01); *G01N 1/4077* (2013.01); *G01N 33/491* (2013.01); *A61B 5/150435* (2013.01); *A61B 5/150442* (2013.01); *A61B 5/150969* (2013.01); *B01L 2200/0631* (2013.01); *B01L 2200/10* (2013.01); *B01L 2300/0681* (2013.01); *B01L 2400/0478* (2013.01); *G01N 2001/4016* (2013.01); *G01N 2001/4088* (2013.01)

(56) References Cited

U.S. PATENT DOCUMENTS

| | | | |
|---|---|---|---|
| 3,640,393 A | | 2/1972 | Hurtig |
| 3,848,579 A | * | 11/1974 | Villa-Real .......... A61B 5/15003 600/577 |
| 4,511,349 A | | 4/1985 | Nielsen et al. |
| 4,627,445 A | | 12/1986 | Garcia et al. |
| 5,055,203 A | | 10/1991 | Columbus |
| 5,163,442 A | | 11/1992 | Ono |
| 5,219,999 A | | 6/1993 | Suzuki et al. |
| 5,364,533 A | * | 11/1994 | Ogura .................... B01D 39/18 210/504 |
| 5,422,018 A | | 6/1995 | Saunders et al. |
| 5,636,640 A | | 6/1997 | Staehlin |
| 5,726,026 A | | 3/1998 | Wilding et al. |
| 5,733,446 A | * | 3/1998 | Holm .................. B04B 1/02 210/206 |
| 5,839,715 A | | 11/1998 | Leinsing |
| 5,922,591 A | | 7/1999 | Anderson et al. |
| 5,979,669 A | * | 11/1999 | Kitajima ............ B01D 39/2017 210/247 |
| 6,074,183 A | | 6/2000 | Allen et al. |
| 6,170,671 B1 | | 1/2001 | Kitajima et al. |
| 6,264,619 B1 | | 7/2001 | Ferguson |
| 6,372,182 B1 | * | 4/2002 | Mauro ............... A61B 10/0045 422/417 |
| 6,506,167 B1 | | 1/2003 | Ishimito et al. |
| 6,869,405 B2 | | 3/2005 | Marsden |
| 8,158,410 B2 | | 4/2012 | Tang et al. |
| 8,163,253 B1 | * | 4/2012 | Hartselle ............ A61B 10/0096 422/400 |
| 2002/0009015 A1 | | 1/2002 | Laugharn, Jr. et al. |
| 2002/0143298 A1 | | 10/2002 | Marsden |
| 2003/0013205 A1 | * | 1/2003 | Konrad ............... B01L 3/50825 436/177 |
| 2003/0134416 A1 | | 7/2003 | Yamanishi et al. |
| 2004/0142463 A1 | | 7/2004 | Walker et al. |
| 2004/0143226 A1 | | 7/2004 | Marsden |
| 2004/0230216 A1 | | 11/2004 | Levaughn et al. |
| 2005/0069459 A1 | | 3/2005 | Ahn et al. |
| 2005/0139547 A1 | * | 6/2005 | Manoussakis ........ B01L 3/5635 210/645 |
| 2005/0214927 A1 | | 9/2005 | Haley |
| 2006/0029923 A1 | | 2/2006 | Togawa et al. |
| 2006/0240964 A1 | | 10/2006 | Lolachi et al. |
| 2007/0031283 A1 | | 2/2007 | Davis et al. |
| 2007/0160503 A1 | | 7/2007 | Sethu et al. |
| 2007/0265549 A1 | * | 11/2007 | Channer .......... A61B 5/150351 600/576 |
| 2008/0135502 A1 | | 6/2008 | Pyo et al. |
| 2008/0240990 A1 | | 10/2008 | Flaherty |
| 2009/0004060 A1 | | 1/2009 | Omuro et al. |
| 2009/0136982 A1 | | 5/2009 | Tang et al. |
| 2009/0181411 A1 | | 7/2009 | Battrell et al. |
| 2009/0204026 A1 | | 8/2009 | Crawford et al. |
| 2010/0089815 A1 | | 4/2010 | Zhang et al. |
| 2010/0093551 A1 | | 4/2010 | Montagu |
| 2010/0198108 A1 | | 8/2010 | Alden |
| 2010/0241031 A1 | | 9/2010 | Lai |
| 2011/0124130 A1 | | 5/2011 | Wagner et al. |
| 2011/0124984 A1 | | 5/2011 | Rostaing |
| 2012/0152858 A1 | | 6/2012 | Yang |
| 2012/0275955 A1 | | 11/2012 | Haghgooie et al. |
| 2012/0277696 A1 | | 11/2012 | Gonzalez-Zugasti et al. |
| 2012/0277697 A1 | | 11/2012 | Haghgooie et al. |
| 2013/0026085 A1 | | 1/2013 | Samsoondar |
| 2013/0040333 A1 | * | 2/2013 | Karlsson ............ A61B 5/15003 435/29 |
| 2013/0052675 A1 | | 2/2013 | Karlsson et al. |
| 2013/0082012 A1 | | 4/2013 | Lean et al. |
| 2013/0086980 A1 | | 4/2013 | Gadini et al. |
| 2013/0175213 A1 | | 7/2013 | Dorrer et al. |
| 2013/0209331 A1 | | 8/2013 | Rodenfels et al. |

FOREIGN PATENT DOCUMENTS

| | | |
|---|---|---|
| CN | 101102847 A | 1/2008 |
| CN | 101332320 A | 12/2008 |
| CN | 102764133 A | 11/2012 |
| DE | 202008010918 U1 | 1/2009 |
| EP | 0376168 A2 | 7/1990 |
| EP | 0747105 A2 | 12/1996 |
| EP | 1096254 A2 | 5/2001 |
| EP | 1106065 A2 | 6/2001 |
| EP | 1477804 A1 | 11/2004 |
| EP | 1602329 A1 | 12/2005 |
| EP | 1627651 A2 | 2/2006 |
| EP | 2264453 A1 | 12/2010 |
| EP | 2413138 A2 | 2/2012 |
| FR | 2929135 A1 | 10/2009 |
| FR | 2977808 A1 | 1/2013 |
| JP | 51162582 | 6/1950 |
| JP | 2004361419 A | 12/2004 |
| JP | 2008302077 A | 12/2008 |
| WO | 9309710 A1 | 5/1993 |
| WO | 2005018710 A2 | 3/2005 |
| WO | 2006047831 A1 | 5/2006 |
| WO | 2007002579 A2 | 1/2007 |
| WO | 2009123592 A1 | 10/2009 |
| WO | 2011040874 A1 | 4/2011 |
| WO | 2012121686 A1 | 9/2012 |

\* cited by examiner

BIOLOGICAL FLUID COLLECTION DEVICE AND BIOLOGICAL FLUID SEPARATION AND TESTING SYSTEM

CROSS REFERENCE TO RELATED APPLICATION

The present application claims priority to U.S. Provisional Application No. 61/811,918, filed Apr. 15, 2013, entitled "Medical Device for Collection of a Biological Sample", the entire disclosure of which is hereby incorporated by reference in its entirety.

BACKGROUND OF THE INVENTION

1. Field of the Disclosure

The present disclosure relates generally to devices, assemblies, and systems adapted for use with vascular access devices. More particularly, the present disclosure relates to devices, assemblies, and systems adapted for collecting biological samples for use in point-of-care testing.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid collection device, such as a blood collection device, that is adapted to receive a multi-component blood sample having a cellular portion and a plasma portion. After collecting the blood sample, the biological fluid collection device is able to separate the plasma portion from the cellular portion. After separation, the biological fluid collection device is able to transfer the plasma portion of the blood sample to a point-of-care testing device. The biological fluid collection device of the present disclosure also provides a closed sampling and transfer system that reduces the exposure of a blood sample and provides fast mixing of a blood sample with a sample stabilizer or preservative. The sample stabilizer or preservative, can be an anticoagulant, or a substance designed to preserve a specific element within the blood such as, for example, RNA, protein analyte, or other element. The biological fluid collection device is engageable with a biological fluid testing device, such as a blood testing device, for closed transfer of a portion of the plasma portion from the biological fluid collection device to the biological fluid testing device. The biological fluid testing device is adapted to receive the plasma portion to analyze the blood sample and obtain test results.

Some of the advantages of the biological fluid collection device and the biological fluid separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to a point-of-care testing device. The biological fluid collection device of the present disclosure enables integrated blood collection and plasma creation in a closed system without centrifugation. The clinician may collect and separate the blood sample and then immediately transfer the plasma portion to the point-of-care testing device without further manipulation. This enables collection and transfer of plasma to the point-of-care testing device without exposure to blood. In addition, the biological fluid collection device of the present disclosure minimizes process time by processing the blood within the biological fluid collection device and without external machinery. Further, for tests which only require small amounts of blood, it eliminates the waste associated with blood collection and plasma separation with an evacuated tube.

In accordance with an embodiment of the present invention, a biological fluid collection device adapted to receive a multi-component blood sample includes a housing defining a first chamber having a first chamber inlet and a first chamber outlet, and a second chamber having a second chamber inlet. The housing also includes a separation member disposed between the first chamber outlet and the second chamber inlet. The first chamber outlet is in communication with the second chamber inlet via the separation member, and the first chamber is adapted to receive the multi-component blood sample. The device also includes an actuator member associated with the second chamber. Actuation of the actuator member in a first direction draws a component of the multi-component blood sample from the first chamber through the separation member to the second chamber.

In certain configurations, the separation member is adapted to allow the component to pass through the separation member to the second chamber. The component may be a plasma component. The device may also include a septum engaged with the housing to seal the first chamber inlet of the first chamber. The device may also include a valve engaged with the second chamber to seal the second chamber. The valve may be transitionable between a closed position in which the second chamber is fully sealed and an open position in which the second chamber is open.

In other configurations, the valve is engageable with a receiving port of a testing device for closed transfer of at least a portion of the component from the second chamber to the testing device. The component may be a plasma component. The valve may also transition from the closed position to the open position via engagement with the receiving port of the testing device. The testing device may be a point-of-care testing device. The valve may be a spring-loaded dispensing valve.

In certain configurations, the housing may include a tubular member removably engaged therewith. The actuator member may be disposable at least partially within the tubular member and the actuator member may be removably engaged with the housing. The tubular member and the actuator member may be removable from the housing after passage of at least a portion of the component from the first chamber into the second chamber. The component may be a plasma component. The device may also include a valve engaged with the second chamber to seal the second chamber. The valve may be transitionable between a closed position in which the second chamber is fully sealed, and an open position in which the second chamber is open. Transition from the closed position to the open position may occur after the tubular member and the actuator member are removed from the housing. The actuator member may include a plunger. The housing may include a sample stabilizer.

In accordance with another embodiment of the present invention, a biological fluid sample separation and testing system, such as a blood sample separation and testing system, for a multi-component blood sample includes a biological fluid collection and separation device, such as a blood collection and separation device. The biological fluid collection and separation device includes a housing defining a first chamber having a first chamber inlet and a first chamber outlet, and a second chamber having a second chamber inlet. The device also includes a separation member disposed between the first chamber outlet and the second chamber inlet. The first chamber is adapted to receive the multi-component blood sample. The system also includes a valve engaged with the second chamber to seal the second chamber. The valve is transitionable between a closed position in which the second chamber is fully sealed, and an open position in which the second chamber is open. The system also includes a testing device having a receiving port adapted to engage the valve of the biological fluid collection and separation device. The valve may be transitioned from the closed position to the open position when the receiving port is engaged with the valve.

In certain configurations, the housing includes a tubular member removably engaged therewith and transition of the valve from the closed position to the open position occurs after the tubular member is removed from the housing. The separation member may be adapted allow a component of the multi-component blood sample to pass through the separation member to the second chamber. The component may be a plasma component. Optionally, the biological fluid sample separation and testing system may include a septum engaged with the housing to seal the first chamber inlet of the first chamber. The valve may be engageable with the receiving port of the testing device for closed transfer of at least a portion of a component from the second chamber to the testing device. The component may be a plasma component and the valve may be a spring-loaded dispensing valve.

The housing may include a tubular member which is removable from the housing after passage of at least a portion of a component of the multi-component blood sample from the first chamber into the second chamber. The component may be a plasma component. The system may also include an actuator member associated with the housing. Actuation of the actuator member in a first direction may draw a component from the first chamber through the separation member to the second chamber. The component may be a plasma component.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood bedside without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

However, the samples provided to such point-of-care testing cartridges are currently manually collected with an open system and transferred to the point-of-care testing cartridge in a manual manner that often leads to inconsistent results, thereby negating the advantage of the point-of-care testing device. Accordingly, a need exists for a system for collecting and transferring a sample to a point-of-care testing device that provides safer, reproducible, and more accurate results. Accordingly, a point-of-care collecting and transferring system of the present disclosure will be described hereinafter. A system of the present disclosure enhances the reliability of the point-of-care testing device by: 1) incorporating a more closed type of sampling and transfer system; 2) minimizing open exposure of the sample; 3) improving sample quality; 4) improving the overall ease of use; and 5) separating the sample at the point of collection.

Figure 4:
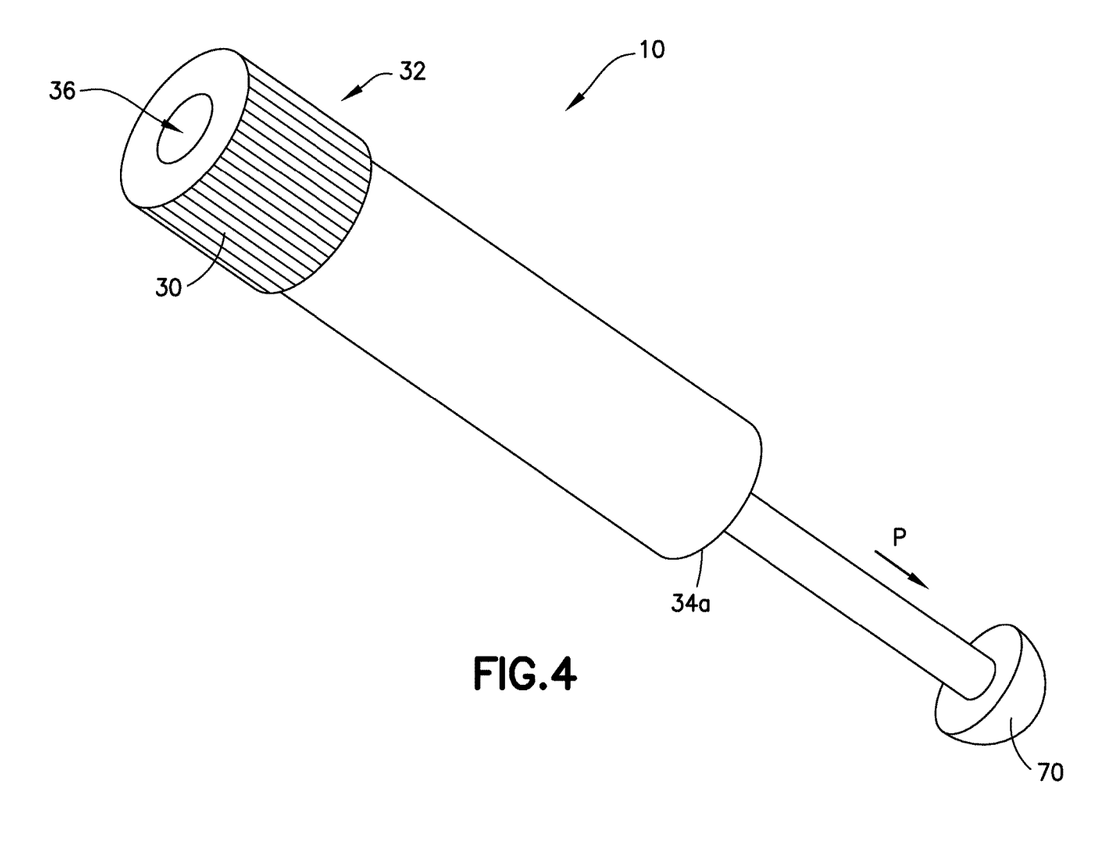
FIG. 4 is a perspective view of a biological fluid collection device in accordance with an embodiment of the present invention, with an actuator member in a second position.
Figure 5:
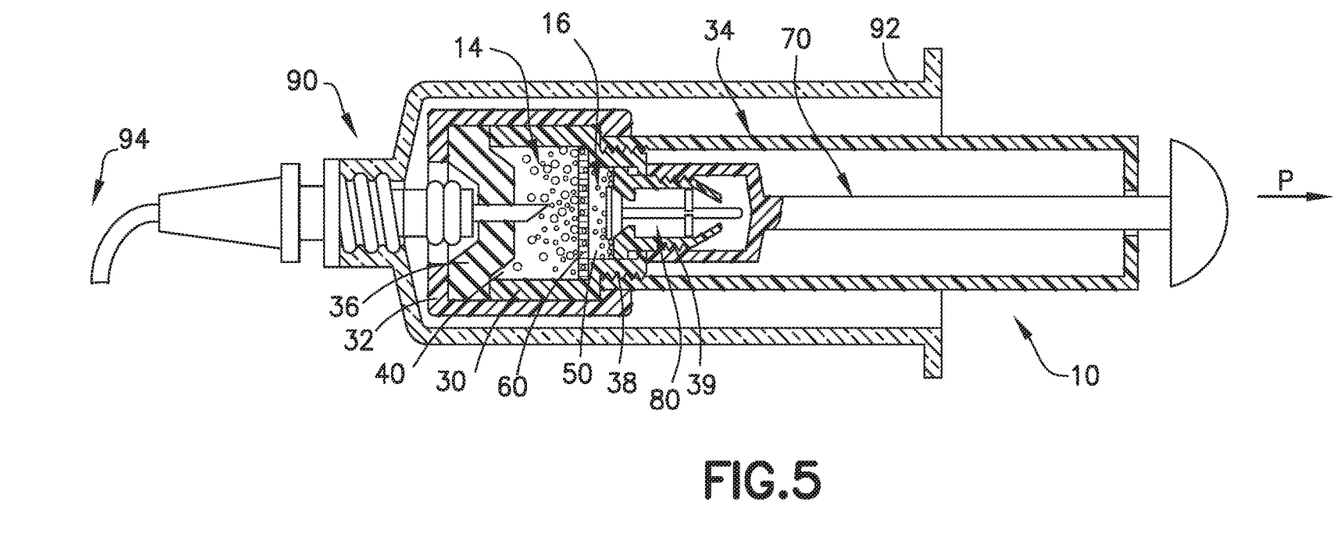
FIG. 5 is a cross-sectional view of the biological fluid collection device engaged with a tube holder in accordance with an embodiment of the present invention.
Figure 6:
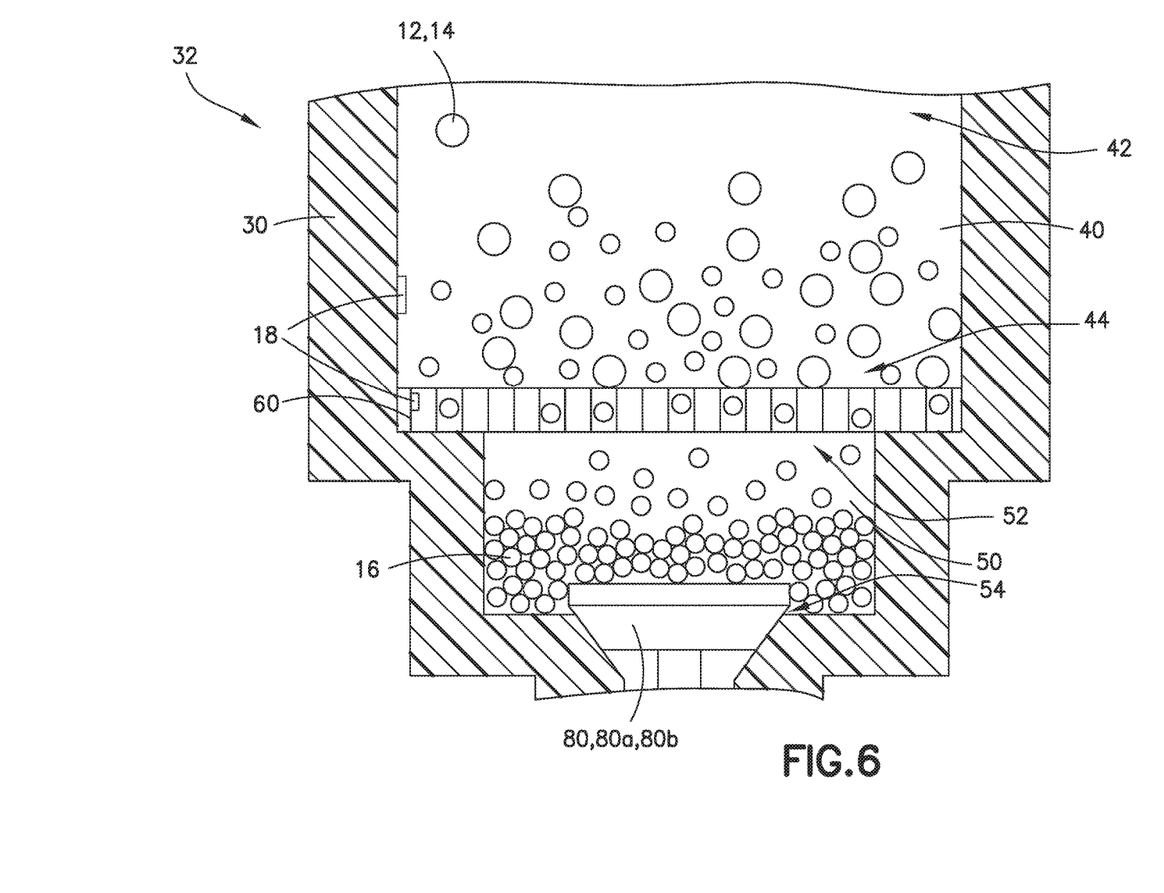
FIG. 6 is a sectional view of the separation member portion of the biological fluid collection device of FIG. 5 in accordance with an embodiment of the present invention, with the separation member separating a plasma portion of a blood sample from a cellular portion of the blood sample.

Reference is now made to FIGS. 1-12 which illustrate a biological fluid collection device, such as a blood collection device, generally indicated as 10, in accordance with an embodiment of the present invention. The blood collection device 10 is configured to collect a multi-component blood sample 12, separate the sample, and supply a portion of the sample to a point-of-care testing device. Specifically, the blood collection device 10 is adapted to receive the multi-component blood sample 12 having a first portion or cellular portion 14 and a second portion or plasma portion 16. After collecting the blood sample 12, the blood collection device 10 is able to separate the plasma portion 16 from the cellular portion 14. After separation, the blood collection device 10 is able to transfer the plasma portion 16 of the blood sample 12 to a point-of-care testing device 22, as shown in FIGS. 7-9 and 12. The blood collection device 10 of the present disclosure also provides a closed separation system that reduces the exposure of a blood sample and provides fast mixing of a blood sample with a sample stabilizer or preservative 18, as illustrated in FIG. 6.

It can be appreciated that the sample stabilizer or preservative 18 can include any one or more of an anticoagulant or a substance, well known in the art that can be used to preserve a specific element within a blood sample, such as RNA, a protein analyte, and the like.

Figure 7:
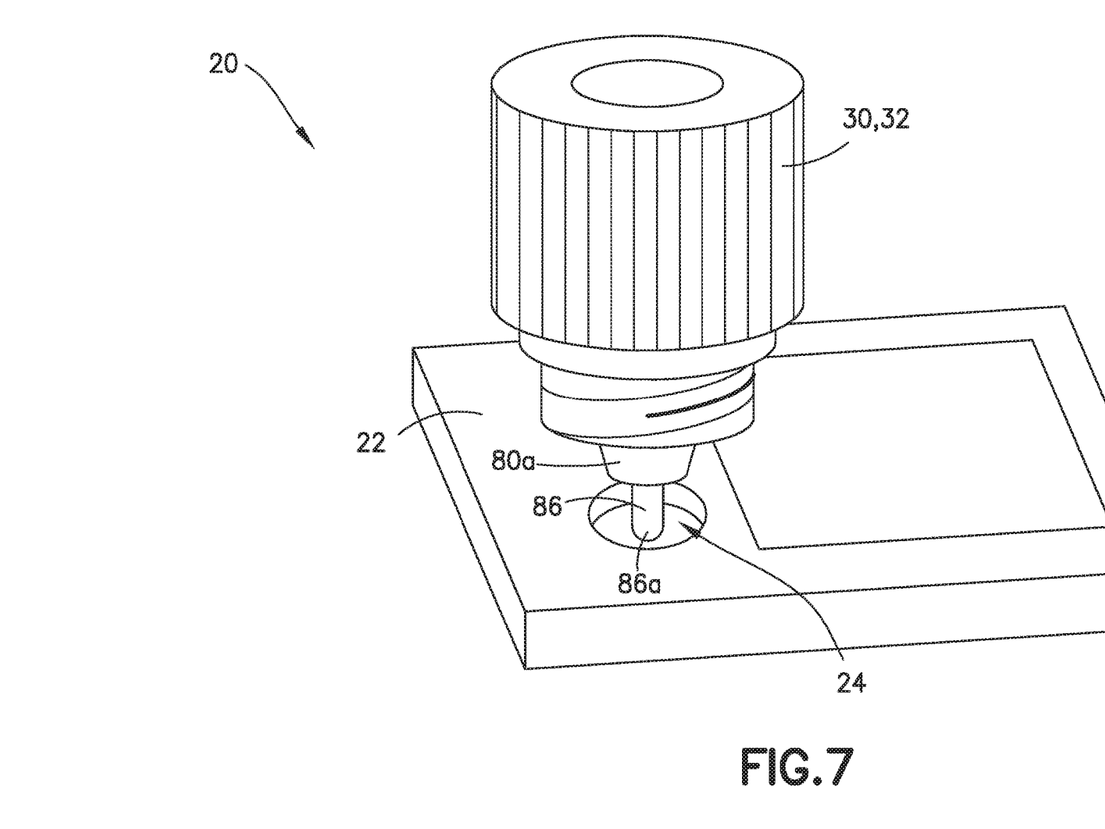
FIG. 7 is a perspective view of a biological fluid collection device and a point-of-care testing device in accordance with an embodiment of the present invention.

Referring in particular to FIG. 7, there is shown an exemplary embodiment of a biological fluid separation and testing system, such as a blood separation and testing system, generally indicated as 20, of the present disclosure which includes the blood collection device 10 and the blood testing device or point-of-care testing device 22 engageable with the blood collection device 10 for closed transfer of a portion of the plasma portion 16 (FIG. 6) from the blood collection device 10 to the blood testing device 22. The blood testing device 22 is adapted to receive the plasma portion 16 to analyze the blood sample and obtain test results.

Figure 3:
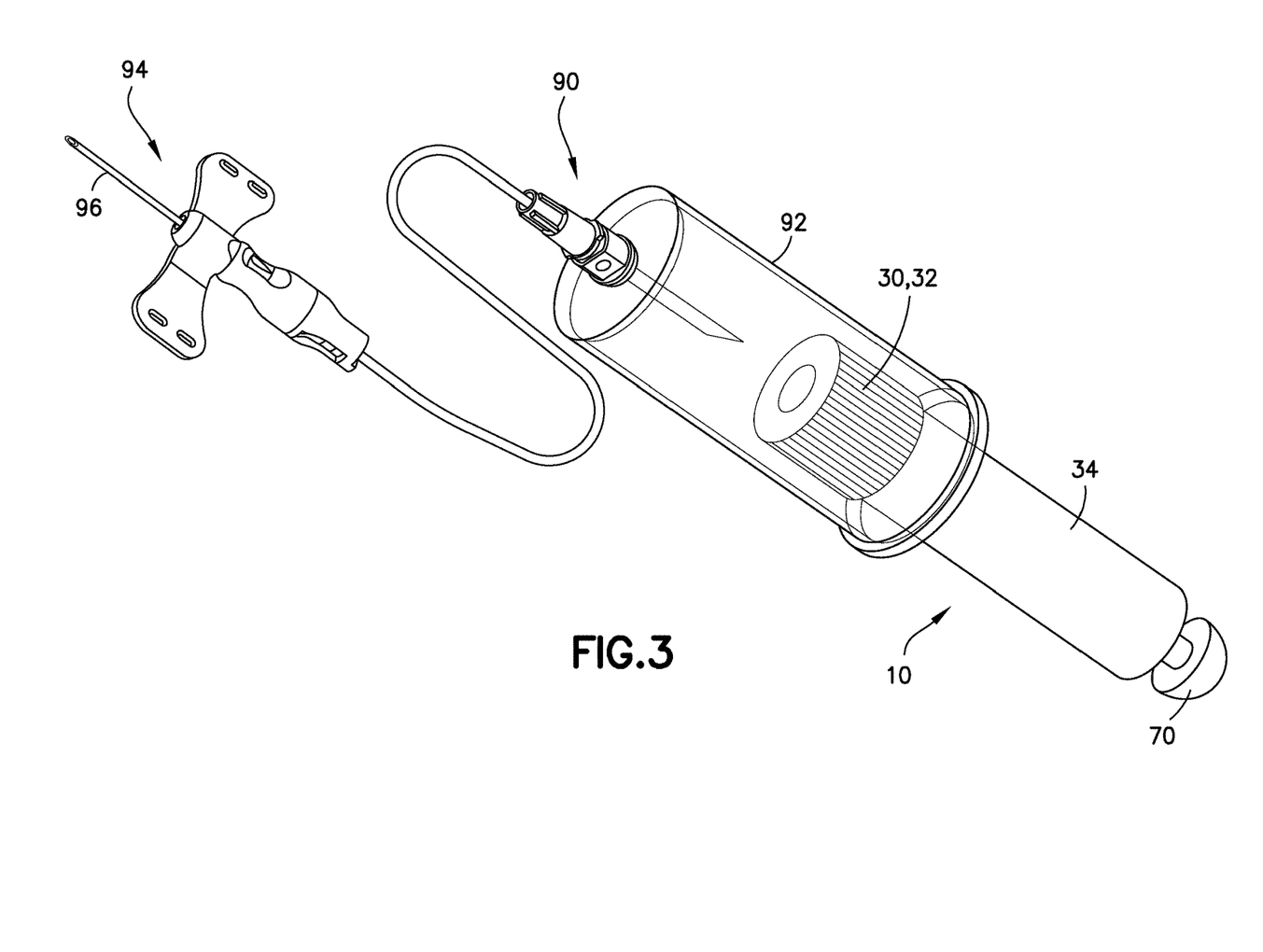
FIG. 3 is a perspective view of a biological fluid collection device in accordance with an embodiment of the present invention, with a biological fluid collection device and a non-patient needle interface.

Referring in particular to FIGS. 1-6, there is shown the biological fluid or blood collection device 10 which is adapted to receive the multi-component blood sample 12 having a cellular portion 14 and a plasma portion 16. The blood collection device 10 includes a housing 30 defining a first chamber 40 having a first chamber inlet 42 and a first chamber outlet 44, and a second chamber 50 having a second chamber inlet 52 and a second chamber outlet 54. The housing 30 further includes a separation member, such as a filter 60, disposed between the first chamber outlet 44 and the second chamber inlet 52 such that the first chamber outlet 44 is in communication with the second chamber inlet 52 via the filter 60. The first chamber 40 is adapted to receive the multi-component blood sample 12. An actuator member 70 is associated with the second chamber 50 such that actuation of the actuator member 70 in a first direction or proximal direction "P", as shown in FIGS. 4 and 5, draws the plasma portion 16 from the first chamber 40 through the filter 60 to the second chamber 50. The actuator member 70 can be in the form of a piston arrangement or plunger, which the clinician can employ, to provide a motivating force for the separation process of the plasma portion 16 from the cellular portion 14.

According to one embodiment, the blood collection device 10 can have an appearance which is similar to the commonly used Vacutainer™ tube manufactured by Becton, Dickinson and Company. More specifically, the blood collection device 10 can includes a cap portion, generally indicated as 32 that defines the housing 30 having an appearance similar to a Hemogard™ cap also manufactured by Becton, Dickinson and Company. The housing 30 can have a tubular member 34 engaged therewith. According to one embodiment, the tubular member 34 can have an appearance similar to the tube portion of the Vacutainer™ tube.

Figure 1:
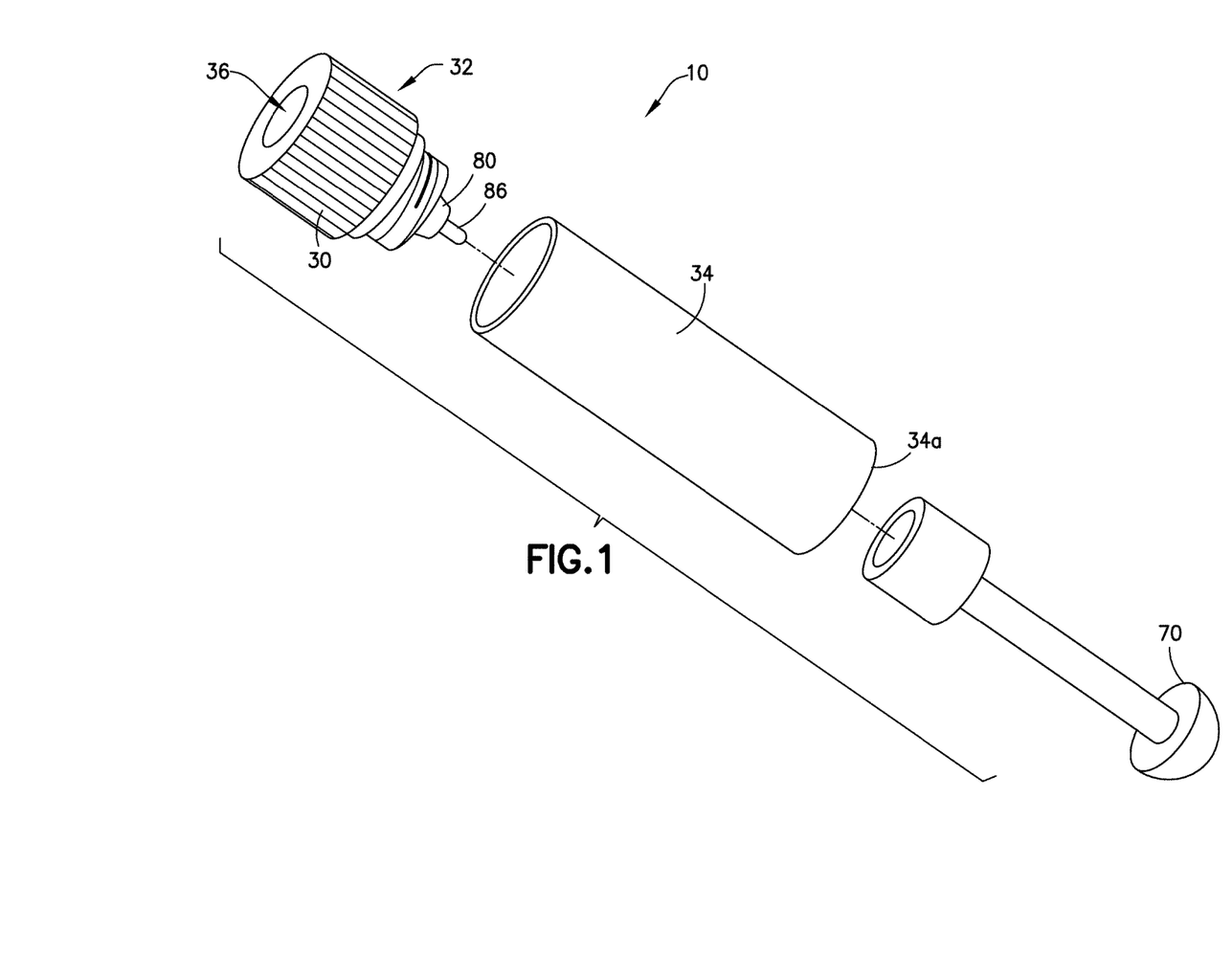
FIG. 1 is an exploded, perspective view of a biological fluid collection device in accordance with an embodiment of the present invention.
Figure 2:
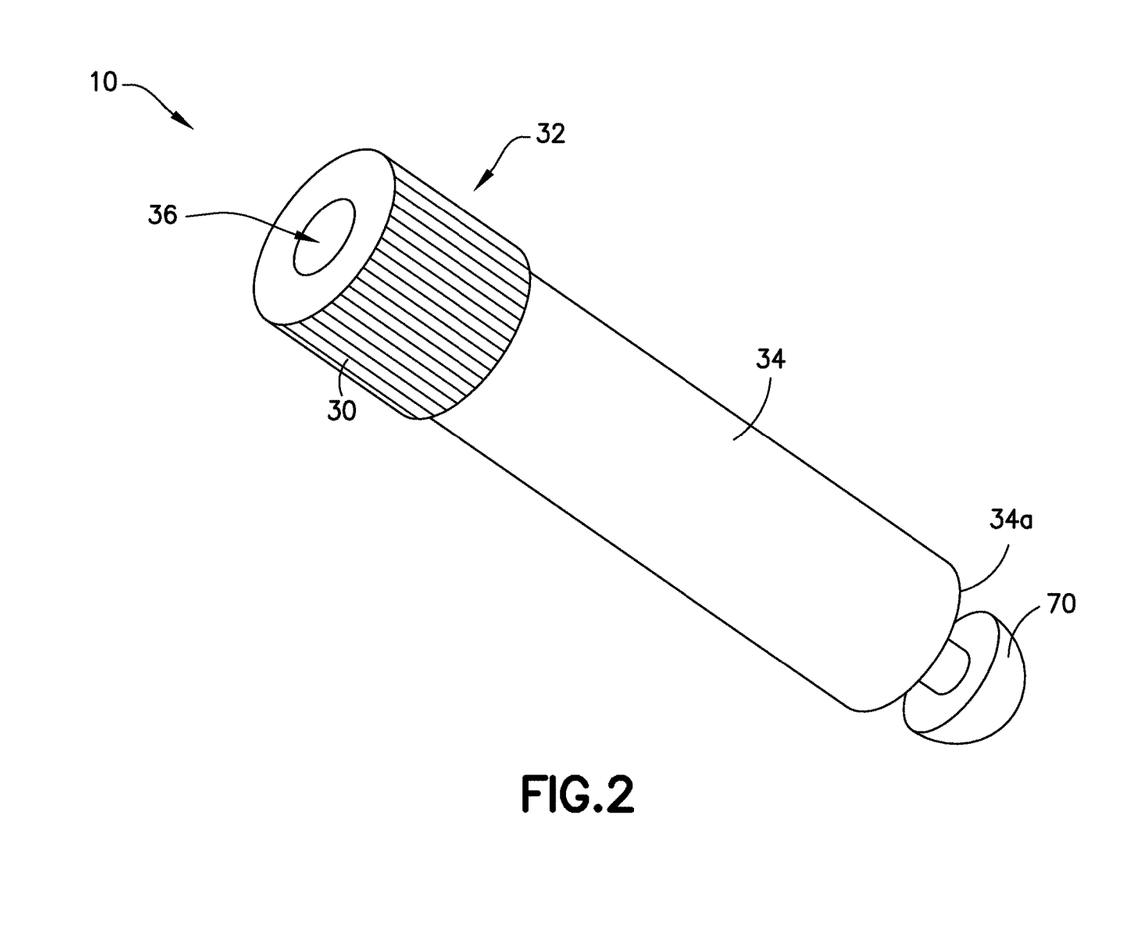
FIG. 2 is an assembled, perspective view of a biological fluid collection device in accordance with an embodiment of the present invention, with an actuator member in a first position.

As shown in FIGS. 1 and 5, the tubular member 34 can be removably engaged with the housing 30/cap 32. According to one embodiment, a first threaded connection 38 can be provided between the tubular member 34 and the cap 32 defining the housing 30. The actuator member 70 can be disposed at least partially within the tubular member 34 and the actuator member 70 can be removably engaged with the housing 30/cap 32 by a second threaded connection 39. The tubular member 34 can be threaded onto a main body of the cap portion 32 while the actuator member 70 can be threaded onto a valve 80 or piston arrangement located within the housing 30/cap 32. The first and second threaded connections 38, 39 enable the tubular member 34 and the actuator member 70 to be removed from the housing 30/cap 32 after passage of at least a portion of the plasma portion 16 from the first chamber 40 into the second chamber 50.

With continuing references to FIGS. 1-5, the cap portion 32 of the device 10 includes a rubber stopper 36 or septum, similar to the Hemoguard™ stopper, engaged with the housing 30 to seal the first chamber inlet 42 of the first chamber 40. The housing 30 for separating the plasma portion 16 from the cellular portion 14 is located under the stopper 36, and employs one of various possible filtration technologies to separate the plasma portion 16 from the cellular portion 14 of the multi-component blood sample 12.

As illustrated in FIG. 3, because the blood collection device 10 has a rubber stopper 36 with the same dimensions as a Vacutainer™ tube, this device 10 would similarly interface with any standard non-patient (NP) needle type interface, as generally shown by 90. Examples of NP needle interfaces would be a tube holder 92 with a finger grip luer adapter (FGLA) attached, with a luer lock access device (LLAD) attached, or with a blood transfer device (BTD) attached, all of which are known in the art and have a standard NP needle interface having a needle covered by a collapsible rubber sleeve. The NP needle interface can be attached to a standard needle assembly/blood collection set, as generally indicated by 94.

With particular reference to FIG. 6, according to one design, the filter 60 is adapted to trap the cellular portion 14 in the first chamber 40 and allow the plasma portion 16 to pass through the filter 60 to the second chamber 50. In one embodiment, the filter 60 may be either hollow fiber membrane filters commercially available, or flat membrane filters, such as track-edge filters commercially available. Membrane filter pore size and porosity can be chosen to optimize separation of clean (i.e., red blood cell free, white blood cell free, and platelet free) plasma 16 in an efficient manner. In another embodiment, the filter 60 can include a lateral flow membrane. In other embodiments, the filter 60 may comprise any filter that is able to trap the cellular portion 14 of the blood sample 12 in the first chamber 40 and allow the plasma portion 16 of the blood sample 12 to pass through the filter 60 to the second chamber 50.

Figure 8:
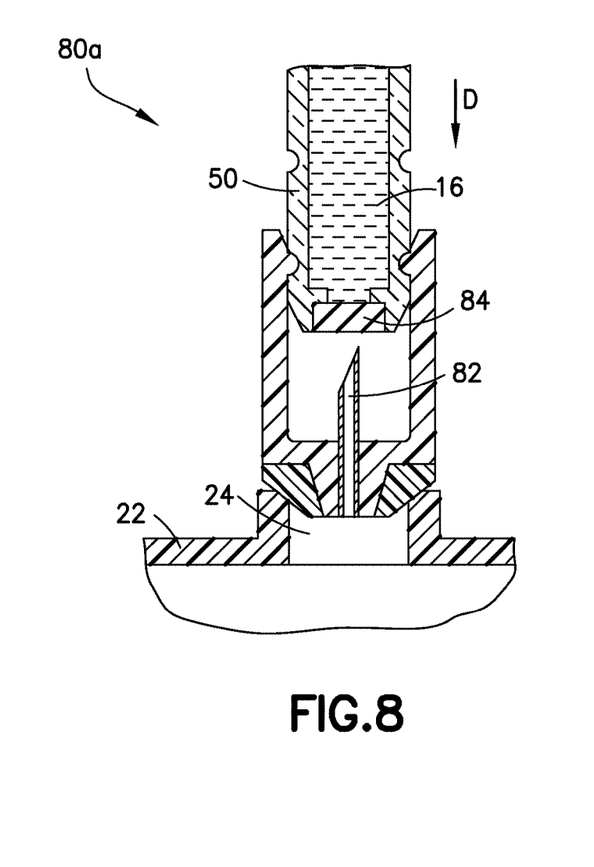
FIG. 8 is a cross-sectional view of a valve of a biological fluid collection device in accordance with an embodiment of the present invention, with the valve in a closed position.
Figure 9:
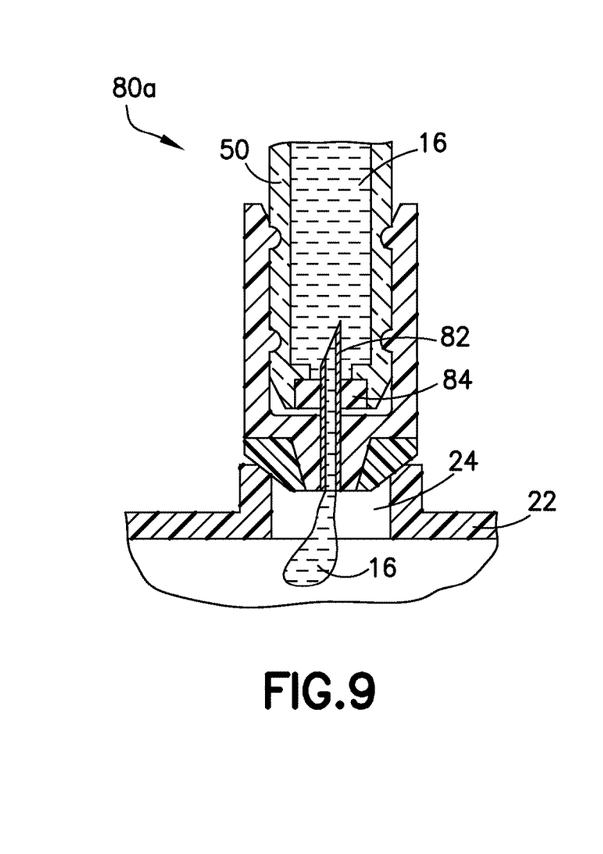
FIG. 9 is a cross-sectional view of a valve of a biological fluid collection device in accordance with an embodiment of the present invention, with the valve in an open position.
Figure 11:
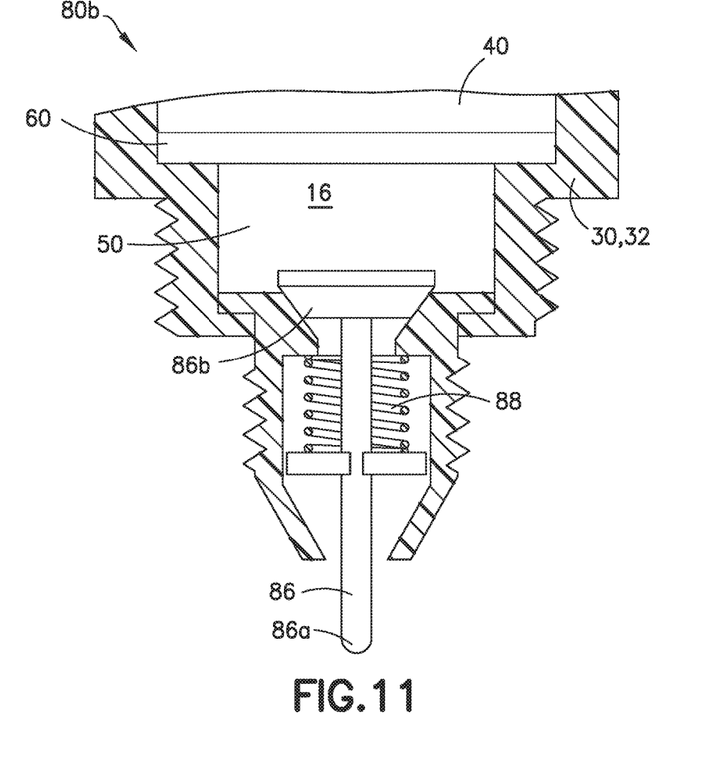
FIG. 11 is a cross-sectional view of a valve of a biological fluid collection device in accordance with another embodiment of the present invention, with the valve in a closed position.
Figure 12:
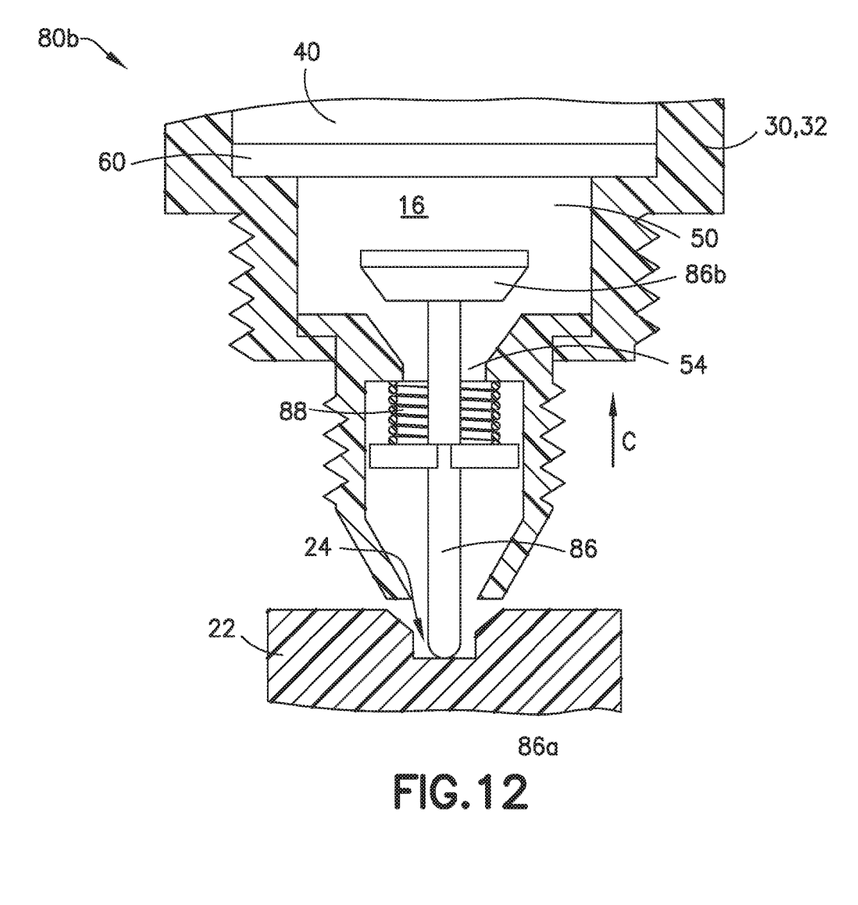
FIG. 12 is a cross-sectional view of a valve of a biological fluid collection device in accordance with another embodiment of the present invention, with the valve in an open position.

With continuing reference to FIGS. 5-6 and with reference to FIGS. 8-9 and 11-12, a dispensing valve 80, 80*a*, 80*b* is engaged with the second chamber 50 to seal the second chamber outlet 54. The valve 80, 80*a*, 80*b* is transitionable between a closed position, such as shown in FIGS. 8 and 11, in which the second chamber 50 is fully sealed and an open position, such as shown in FIGS. 9 and 12, in which the second chamber 50 is open.

As shown in FIGS. 7-9 and 12, when the valve 80, 80*a*, 80*b* is engaged with a receiving port 24 of a testing device, such as a point-of-care testing device 22, closed transfer of at least a portion of the plasma portion 16 from the second chamber 50 to the testing device 22 occurs. Specifically, the valve 80, 80*a*, 80*b* can be configured to transition from the closed position to the open position via engagement with the receiving port 24 of the testing device 22. This transition from the closed position to the open position occurs after the tubular member 34 and the actuator member 70 are removed from the housing 30.

According to one embodiment, as shown in FIGS. 8-9, the valve 80*a* can be a universal delivery valve having a design wherein the plasma portion 16 is dispensed into the point of care testing device 22 when the cap 32 is pushed in a distal direction "D". Applying the distal force "D" to the cap causes a transfer device, such as a needle cannula 82, to penetrate a sealing member 84, which seals the second chamber 50 of the housing, and allows the plasma portion to flow therethrough and into the testing device 22.

Figure 10:
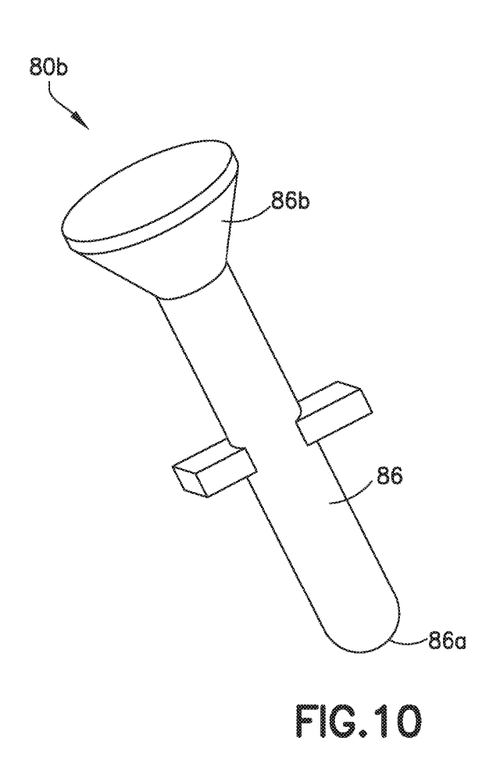
FIG. 10 is a perspective view of a valve of a biological fluid collection device in accordance with another embodiment of the present invention.

According to another design, as shown in FIGS. 10-12, the dispensing valve 80*b* may be similar to a Schrader type valve or may be of some other design where the plasma would be dispensed into the point-of-care testing device 22 when a force in the distal direction "D" is applied to the cap 32. The dispensing valve 80*b* includes a valve stem 86 biased by a spring 88 so that application of a force to the cap 32 in the distal direction "D" causes an end 86*a* of the valve stem to contact the receiving port 24 of the point-of-care testing device 22. This force results in a compressive force "C" being applied to the valve stem 86 so that the spring 88 compresses and a valve cap 86*b* of the dispensing valve 80*b* enters into the second chamber 50 so that the second chamber outlet 54 opens up, as shown in FIG. 12, allowing the plasma portion 16 to flow therethrough and into the receiving port 24 of the point-of-care testing device 22.

The housing 30 of the biological fluid collection device 10 may also include a sample stabilizer or preservative 18. The sample stabilizer 18, can be an anticoagulant, or a substance designed to preserve a specific element within the blood such as, for example, RNA, protein analyte, or other element. In one embodiment, a layer of sample stabilizer 18 may be disposed adjacent a wall portion of the first chamber 40 or within the first chamber inlet 42. In other embodiments, the sample stabilizer 18 may be located adjacent the filter 60 or any other area of the blood collection device 10 in which it contacts a biological sample.

With reference to FIGS. 3-4, the operation of the device 10 is as follows: 1) Initially, a blood collection set 94 of choice, such as a needle/hub type or a wing set type is attached to one of the NP needle interfaces 90 discussed above; 2) Next, the patient is stuck with a needle 96 of the blood collection set 94; 3) Instead of using an evacuated tube such as the Vacutainer™ tube, the biological fluid collection device 10 of the invention is inserted into the holder 92 into contact with the NP needle interface 90. A small volume of blood would be drawn from the patient into the first chamber 40 of the housing 30 of the device 10; 4) Thereafter, the device 10 is removed from the holder 92; 5) Then, the clinician applies a pulling or proximal force "P" on the actuator member/plunger rod 70 extending through an end portion 34*a* of the tubular member 34, as shown in FIG. 4. This action causes the multi-component blood sample 12 to be pulled through the filter 60 located between the first chamber 40 and the second chamber 50 to separate out the plasma portion 16 and draw the plasma portion 16 into the second chamber 50; 6) Next, the clinician separates the cap 32 of the device 10 from the tubular member 34 by unscrewing the tubular member 34 and actuator member/plunger rod 70 therefrom; and 7) Finally, the cap 32 is used by the clinician to dispense the plasma into a point-of-care testing device 22 by aligning the dispensing valve 80 with a port or well 24 of the point-of-care testing device 22 and pushing the cap portion 32 in a distal direction one or more times to cause the valve to open up and dispense the plasma portion 16 through the second chamber outlet 54 into the testing device 22.

Some of the advantages of the blood collection device and the blood separation and testing system of the present disclosure over prior systems are that it is a closed system which reduces blood sample exposure, it provides passive and fast mixing of the blood sample with a sample stabilizer, it facilitates separation of the blood sample without transferring the blood sample to a separate device, and it is capable of transferring pure plasma to a point-of-care testing device. The blood collection device of the present disclosure enables integrated blood collection and plasma creation in a closed system without centrifugation. The clinician may collect and separate the blood sample and then immediately transfer the plasma portion to the point-of-care testing device without further manipulation. This enables collection and transfer of plasma to the point-of-care testing device without exposure to blood. In addition, the blood collection device of the present disclosure minimizes process time by processing the blood within the blood collection device and without external machinery. Further, for tests which only require small amounts of blood, it eliminates the waste associated with blood collection and plasma separation with an evacuated tube.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid collection device for receiving a multi-component blood sample, the biological fluid collection device comprising:
a housing defining a first chamber having a first chamber inlet and a first chamber outlet, a second chamber having a second chamber inlet and a second chamber outlet, and including a separation member disposed between the first chamber outlet and the second chamber inlet, wherein the first chamber outlet is in communication with the second chamber inlet via the separation member, wherein the first chamber receives the multi-component blood sample;
an actuator member comprising a plunger rod and a piston including a valve,
wherein at least a portion of the piston is located within the housing and movement of the actuator member in a first direction draws a component of the multi-component blood sample from the first chamber through the separation member to the second chamber,
wherein the valve transitions between a closed position in which the second chamber is fully sealed and an open position in which the second chamber is open.

2. The biological fluid collection device of claim 1, wherein the separation member allows the component to pass through the separation member to the second chamber.

3. The biological fluid collection device of claim 2, wherein the component is a plasma component.

4. The biological fluid collection device of claim 1, further comprising a septum engaged with the housing to seal the first chamber inlet of the first chamber.

5. The biological fluid collection device of claim 1, wherein the valve engages a receiving port of a testing device for closed transfer of at least a portion of the component from the second chamber to the testing device.

6. The biological fluid collection device of claim 5, wherein the component is a plasma component.

7. The biological fluid collection device of claim 5, wherein the valve transitions from the closed position to the open position via engagement with the receiving port of the testing device.

8. The biological fluid collection device of claim 5, wherein the testing device comprises a point-of-care testing device.

9. The biological fluid collection device of claim 1, wherein the valve is a spring-loaded dispensing valve.

10. The biological fluid collection device of claim 1, wherein the actuator member is disposable at least partially within a tubular member and wherein at least a portion of the actuator member is removably engaged with the housing.

11. The biological fluid collection device of claim 10, wherein the tubular member and at least a portion of the actuator member are removable from the housing after passage of at least a portion of the component from the first chamber into the second chamber.

12. The biological fluid collection device of claim 11, wherein the component is a plasma component.

13. The biological fluid collection device of claim 11, wherein transition of the valve from the closed position to the open position occurs after the tubular member and at least a portion of the actuator member are removed from the housing.

14. The biological fluid collection device of claim 1, wherein the housing includes a sample stabilizer.

15. A biological fluid sample separation and testing system for a multi-component blood sample, comprising:
a biological fluid collection and separation device comprising:
a housing defining a first chamber having a first chamber inlet and a first chamber outlet, a second chamber having a second chamber inlet and a second chamber outlet, and including a separation member disposed between the first chamber outlet and the second chamber inlet, wherein the first chamber is in communication with the second chamber inlet via the separation member, wherein the first chamber receives the multi-component blood sample; and
an actuator member comprising a plunger rod and a piston including a valve,
wherein at least a portion of the piston is located within the housing and movement of the actuator member in a first direction draws a component of the multi-component blood sample from the first chamber through the separation member to the second chamber,
wherein the valve transitions between a closed position in which the second chamber is fully sealed, and an open position in which the second chamber is open; and a testing device having a receiving port adapted to engage the valve of the biological fluid collection and separation device, wherein the valve transitions from the closed position to the open position when the receiving port is engaged with the valve.

16. The biological fluid sample separation and testing system of claim 15, wherein the housing includes a tubular member removably engaged therewith and transition of the valve from the closed position to the open position occurs after the tubular member is removed from the housing.

17. The biological fluid sample separation and testing system of claim 15, wherein the separation member allows a component of the multi-component blood sample to pass through the separation member to the second chamber.

18. The biological fluid sample separation and testing system of claim 17, wherein the component is a plasma component.

19. The biological fluid sample separation and testing system of claim 15, further comprising a septum engaged with the housing to seal the first chamber inlet of the first chamber.

20. The biological fluid sample separation and testing system of claim 15, wherein the valve is engageable with the receiving port of the testing device for closed transfer of at least a portion of a component of the multi-component blood sample from the second chamber to the testing device.

21. The biological fluid sample separation and testing system of claim 20, wherein the component is a plasma component.

22. The biological fluid sample separation and testing system of claim 15, wherein the valve is a spring-loaded dispensing valve.

23. The biological fluid sample separation and testing system of claim 15, wherein the housing includes a tubular member which is removable from the housing after passage of at least a portion of a component of the multi-component blood sample from the first chamber into the second chamber.

24. The biological fluid sample separation and testing system of claim 23, wherein the component is a plasma component.

25. The biological fluid sample separation and testing system of claim 18, wherein actuation of the actuator member in a first direction draws a component of the multi-component blood sample from the first chamber through the separation member to the second chamber.

26. The biological fluid sample separation and testing system of claim 25, wherein the component is a plasma component.

* * * * *